United States Patent [19]

Inukai et al.

[11] 4,371,484

[45] Feb. 1, 1983

[54] PROCESS FOR MAKING POROUS SINTERED BODY OF CALCIUM PHOSPHATE

[75] Inventors: Takao Inukai; Yoshiaki Fukuda; Mikiya Ono, all of Yokoze, Japan

[73] Assignee: Mitsubishi Mining & Cement Co., Ltd., Tokyo, Japan

[21] Appl. No.: 267,970

[22] Filed: May 27, 1981

[30] Foreign Application Priority Data

Jun. 13, 1980 [JP] Japan .................. 55-78919

[51] Int. Cl.³ ........................... B29H 7/20
[52] U.S. Cl. ...................... 264/44; 264/69; 264/81; 264/221; 264/311; 264/317
[58] Field of Search ............. 264/44, 49, 69, 81, 264/221, 311, 317, DIG. 44; 106/41

[56] References Cited

U.S. PATENT DOCUMENTS

| | | | |
|---|---|---|---|
| 3,090,094 | 5/1963 | Schwartzwalder | 264/DIG. 44 |
| 3,326,787 | 6/1967 | Jacobs | 264/69 |
| 3,396,952 | 8/1968 | Jennrich et al. | 264/44 |
| 3,907,579 | 9/1975 | Ravault | 264/44 |
| 3,939,002 | 2/1976 | Washbourne | 264/44 |
| 4,004,933 | 1/1977 | Ravault | 501/81 |
| 4,149,894 | 4/1979 | Ebihara et al. | 106/39.5 |

FOREIGN PATENT DOCUMENTS 1455360 11/1976 United Kingdom .

OTHER PUBLICATIONS

Kyobashi, Chuo-Ku, Bridgestone Tire Co., Ltd., Tokyo, Japan, May 9, 1977.
Kanebo Chemicals Co. Ltd., Dec. 1975.

*Primary Examiner*—Donald E. Czaja
*Assistant Examiner*—W. Thompson
*Attorney, Agent, or Firm*—Jordan and Hamburg

[57] ABSTRACT

A process for making a porous sintered body of calcium phosphate having continuous and fine pores distributed uniformly throughout the porous body is provided which comprises the steps of: preparing a slurry of amorphous calcium phosphate having a molar ratio of calcium to phosphor ranging within 1.59 to 1.80; adding a foaming agent to said slurry; dipping a porous body of an organic material having continuous and fine void channels into said slurry prior to or after foaming said slurry to allow said slurry to adhere on the internal walls of said void channels; heating said porous body of said organic material at a temperature high enough for decomposing said organic material to varnish into smoke and concurrently for thermally converting said amorphous calcium phosphate into hydroxyapatite to form a network of hydroxyapatite; and sintering said network of hydroxyapatite to form said porous sintered body.

15 Claims, No Drawings

PROCESS FOR MAKING POROUS SINTERED BODY OF CALCIUM PHOSPHATE

BACKGROUND OF THE INVENTION

1. Field of the Invention

The present invention relates to a process for making a porous body of calcium phosphate, and more particularly to a process for making a porous sintered body of calcium phosphate having continuous and fine pores distributed uniformly throughout the body.

2. Prior Art

Porous bodies of ceramics, including a porous body of calcium phosphate, have hitherto been used for fillers to be filled in defects or hollow portions of bones, carriers for carrying catalysts or filter materials. Reference should be made to, for example, British Pat. No. 1,455,360, U.S. Pat. No. 4,149,894, U.S. patent application Ser. No. 191,894 now abandoned, Apr. 1, 1982, and U.S. patent application Ser. No. 261,085 filing date May 7, 1981. In the known process for making a porous body of ceramics, an organic porous body made of foamed polyurethane and having continuous void channels is dipped into a slurry of a material for ceramics to allow the slurry to adhere on the internal walls of the continuous void channels, and then the organic porous body is heated to decompose the organic material forming the porous body and concurrently to sinter the adhering material for ceramics to obtain a porous sintered body of ceramics. However, in this known process, a certain portion of the void channel in the organic porous body frequently gets clogged by the slurry of the material for ceramics. Once some portion of the void channel has gotten clogged, the slurry is prevented from getting deeper into the channel beyond the clogged portion. As a result of uneven distribution of slurry in the void channels of the organic porous body, it is difficult to obtain a porous sintered body of ceramics having continuous pores distributed uniformly throughout the resultant porous ceramic body. The tendency of clogging is disadvantageously increased as the void channels of the organic porous body become finer. In the extreme case, a slurry of ceramic material can scarcely adhere on nowhere of the internal walls of the void channels. Due to this clogging problem, a porous body of ceramics having continuous pores of very small dimension could not be made by the known process.

In order to solve this clogging problem, it has been proposed to apply a centrifugal force to the organic porous body after dipping the same into the slurry of ceramic material or to squeeze the organic porous body through a roller assembly. However, by these centrifugalizing or squeezing methods, it was difficult to remove the slurry of ceramic material only at the clogged portion. When treated by such methods, considerable parts of the slurry of ceramic material adhering on the internal walls of the void channels of the organic porous body are removed, leading to reduction in strength of the resultant porous body of ceramics. Thus, the network of the porous sintered body of ceramics thus produced is so weak that it cannot withstand the external forces applied in practical use.

With the aim to improve the strength of the finished product of ceramic material, it has been tried to use finer particles of ceramic material in preparation of the slurry.

However, when the viscosity of the slurry is increased by using the particles of smaller size, the slurry will adversely aggravate the tendency of clogging. On the other hand, if the ceramic particles of coarser size are used to lower the density of slurry, the strength of the resultant porous body of ceramics is reduced. Thus, increase in strength of the porous body conflicts with prevention of clogging in the preparation step, and these conflicting requirements cannot be satisfied by varying the particle size of the ceramic material.

It has been further proposed to process the internal walls of the void channels of the organic porous body in order to allow the walls to be rugged so as to improve the adsorption property thereof for holding the slurry of ceramic material. This proposal involves a disadvantage that an additional processing step is necessitated. Nevertheless, the problem of clogging of the slurry of ceramic material in fine channels of the organic porous body cannot be solved by this proposal.

As has been mentioned above, in any of the known processes for making a porous ceramic body, the slurry of ceramic material cannot adhere uniformly on the walls of fine void channels of the organic porous body due to the clogging problem. In accordance with any of the prior art process, it is impossible to make a porous sintered body of ceramics having continuous and fine pores distributed uniformly throughout the porous body and having a satisfactory strength.

OBJECTS AND SUMMARY OF THE INVENTION

A primary object of the present invention is to allow the slurry of amorphous calcium phosphate to adhere on the internal walls of finer void channels of the organic porous body without suffering clogging in preparation of a porous sintered body of calcium phosphate having continuous and fine pores.

Another object of the present invention is to provide a process for making a porous sintered body of calcium phosphate having continuous and fine pores distributed uniformly throughout the porous body.

A further object of the present invention is to provide a process for making a porous sintered body of calcium phosphate having a strength high enough for practical uses.

The above and other objects of the present invention will become apparent from the following description.

According to the present invention, there is provided a process for making a porous sintered body of calcium phosphate having continuous and fine pores distributed uniformly throughout the porous body, comprising the steps of preparing a slurry of amorphous calcium phosphate having a molar ratio of calcium to phosphor ranging within 1.59 to 1.80, adding a foaming agent to said slurry, dipping a porous body of an organic material having continuous and fine void channels into said slurry prior to or after foaming said slurry to allow said slurry to adhere on the internal walls of said void channels, heating said porous body of said organic material at a temperature high enough for decomposing said organic material to vanish into smoke and concurrently for thermally converting said amorphous calcium phosphate into hydroxyapatite to form a network of hydroxyapatite, and sintering said network to form the porous sintered body.

DESCRIPTION OF THE INVENTION

The amorphous calcium phosphate used in the present invention gives an X-ray diffraction image including wide and blurred halos showing the absence of regular arrangement of atoms or showing that the atoms are arranged regularly only at narrow localized portions. Such a slurry of amorphous calcium phosphate can be prepared by the known wet synthesis process, wherein a solution containing phosphoric ions is added to a solution containing calcium ions or a suspension of a calcium compound so that the molar ratio of calcium to phosphor is maintained within the range of 1.59 to 1.80. Excess water of the thus obtained solution of calcium phosphate can be removed by dehydration or drying at about 100° C. followed by addition of an appropriate dispersion medium to prepare the slurry of amorphous calcium phosphate to be used in the process of this invention. It is essential that the molar ratio of calcium to phosphor of the slurry be within the range of 1.59 to 1.80. If the molar ratio of calcium to phosphor is less than 1.59. the content of hydroxyapatite in the finished product becomes less than 50%. On the contrary, if the molar ratio of calcium to phosphor is more than 1.80, the finished product is not adapted for practical uses because CaO is formed at the sintering step.

The particles of amorphous calcium phosphate contained in the slurry prepared in accordance with the aforementioned wet process are very fine. The particle size is so fine that the average particle size is about 0.05 microns and the maximum particle size is about 0.5 microns. As the particle size becomes smaller, the surface area becomes larger and the cohesive power of the slurry becomes stronger. By the use of a slurry containing finer particles of amorphous calcium phosphate, the strength of the porous body of amorphous calcium phosphate, after the step of thermally decomposing the organic porous body and prior to the sintering step, is increased due to increase in cohesive power of the slurry. The wet synthesis process is preferred because the particle size, shape and particle size distribution of the particles of calcium phosphate can be easily controlled and the viscosity of the slurry can be readily changed to prepare a slurry which is improved in adhesive property and has a thixotropic property.

In accordance with an important aspect of this invention, a foaming agent is added to the aforementioned slurry of amorphous calcium phosphate, and the porous carrier body of an organic material is dipped into the slurry prior to or after foaming said slurry. The slurry can be foamed simply by stirring the slurry or by compressing and then expanding the porous body of the organic material while dipping the latter into the slurry. The addition of a foaming agent is an important characteristic feature of this invention. Very fine foams are formed in the slurry of calcium phosphate by the addition of the foaming agent. Since these very fine foams get into the fine void channels of the organic porous body, the channels are prevented from being filled by dense slurry to be clogged.

Fine foams of the slurry getting into the void channels of the organic porous body are combined with each other and some of them are broken as they contact with the walls of the channels to adhere onto the walls. As a result, the overall surface area of the channels is covered by the aggregated foams of the slurry. The adhesive property of the slurry is improved when any of the surfactants referred to hereinafter is used as the foaming agent. If the size of foams is small, the dipping step is operated under a reduced pressure to expand the foams greater thereby to facilitate formation of continuous aggregation of foams over the entire surface area of the internal walls of the channels. After dipping into the foamed slurry or after foaming the slurry subsequent to dipping the organic porous body thereinto, the porous body of organic material may be treated by a centrifugal separator or through a roller assembly in order to control the amount of the slurry adhering on the walls of the void channels. However, even when subjected to such a centrifugalizing or squeezing treatment, the foams of the slurry are retained in the channels so that immoderate removal of the slurry, otherwise experienced in the prior art process, is prevented.

Although the foams of the slurry are combined together to form continuous bubbled films covering over the walls of the channels and some of the foams contacting with the surface of the walls are broken to adhere onto the walls, as mentioned above, continuous films adhereing intimately onto the walls of the channels are not yet formed at this stage. All of the foams are broken at the subsequent heating step at which the dispersion medium of the slurry is evaporated and amorphous calcium phosphate adheres onto the internal walls of the void channels to form a continuous network of calcium phosphate. The organic material forming the carrier porous body is decomposed to vanish into smoke by heating generally at about 500° C., so that a network of amorphous calcium phosphate is left. Prior to the heating step, the foams may be broken by exposing to ether vapor or by subjecting to ultrasonic waves.

By heating amorphous calcium phosphate at a temperature higher than 800° C., rearrangement in crystal structure occurs so that amorphous calcium phosphate is thermally converted into hydroxyapatite.

Due to this rearrangement in crystal structure, sintering is further promoted to give hydroxyapatite of higher strength.

Although the upper limit of the sintering temperature is not critical provided that calcium phosphate is not decomposed or melted, it is preferred that the sintering temperature be lower than 1400° C. from the economical point of view.

Examples of preferred organic porous bodies having continuous and fine void channels and used in this invention are polyurethane sponges and sponges of vinyl polymers. It is desired that the cross-sectional dimension of the void channels of the organic porous body ranges within 0.05 to 1.5 mm, preferably within 0.1 to 0.7 mm. If the cross-sectional dimension at any portion of the channels is less than 0.05 mm, such a portion is apt to be clogged by the slurry of calcium phosphate. On the contrary, if the cross-sectional dimension at any portion of the channels exceeds 1.5 mm, the strength of the corresponding portion of the finished porous body of calcium phosphate is lowered to an unsatisfactory level.

The foaming agents added to the slurry of amorphous calcium phosphate include surfactants having the foaming properties. The surfactants usable in this invention include anionic surfactants, cationic surfactants, non-ionic surfactants and non-aqueous dispersion medium surfactants.

The anionic surfactants include fatty acid soaps such as sodium laurate, sodium myristate, and sodium oleate, alkyl sulfates such as sodium decylsulfate and sodium hexadecylsulfate, and straight-chain alkylbenzenesulfates. The cationic surfactants include quaternary ammonium salts such as benzildimethylalkylammonium chloride and dodecyldimethylbenzilammonium bromide, and amine salts such as diethylaminoethyloleylamide. Non-ionic surfactants include polyoxyethylene alkyl ethers such as ethylene oxide addition products of lauryl alcohol, stearyl alcohol and cetyl alcohol, polyoxyethylene sorbitan monoalkyl esters such as sorbitan monolaurate polyglycol ether and sorbitan monooleate polyglycol ether, and sugar esters. The non-aqueous dispersion medium surfactants include fatty acid dodecyl ammonium and sodium dioctylsulfosuccinate.

The sintered body of ceramics obtainable by the process of this invention is strong enough for practical uses and has continuous and fine pores distributed uniformly throughout the porous body, the cross-sectional dimension in every direction of each of said pores ranging within 0.03 to 1.2 mm and the porosity of the porous body ranging within 40 to 97%. The porous body of calcium phosphate obtained in accordance with the process of this invention can be used not only as a filter and a carrier for catalysts but also for biological applications including uses as a carrier for culture media for cultivating microorganisms or living cells and as an implantation material for filling in a defect or hollow portion of bones or for substituting for the cut-off bones.

EXAMPLES OF THE INVENTION

The present invention will now be described in detail by referring to some examples thereof.

EXAMPLE 1

A solution of phosphoric acid was dropwisely added to a suspension of calcium hydroxide and the pH value of the reaction mixture was adjusted to prepare suspensions of amorphous calcium phosphate having, respectively, the molar ratio of calcium to phosphor of 1.59, 1.67 and 1.80. Each of these suspensions was dehydrated and dried to obtain calcium phosphate of powder form which was pulverized finely. The pulverized powders were added with water to prepare calcium phosphate slurries A, B and C. Separately, calcium hydrogenphosphate and calcium carbonate were mixed together in a predetermined ratio, and the mixture was calcined at 1300° C. for 2 hours to prepare hydroxyapatite. The thus obtained hydroxyapatite was added with water and put into a pot mill where it was pulverized for one day to prepare a hydroxyapatite slurry D.

One part, by weight, of polyoxyethylene sorbitan monolaurate was added to 100 parts, by weight, of each of the aforementioned slurries as the foaming agent. A polyurethane sponge having continuous void channels, the average cross-sectional dimension of the channels being 0.5 mm, was dipped into each of the slurries. The sponge was repeatedly compressed and then allowed to expand in each slurry to allow the slurry to get into the channels and to be foamed therein. Each of the sponges impregnated with respective slurries was dried at 100° C. for a day, and then sintered at 1110° C. for 2 hours to decompose the polyurethane by heating and concurrently to sinter calcium phosphate to obtain a sintered porous body.

The sintered porous bodies obtained from the slurries A, B and C has continuous pores (Average Cross-sectional Dimension of Pores: 0.35 mm, Porosity: 90%) including few closed-cells. According to the X-ray diffractiometry, it had been found that almost all parts of the porous networks obtained from the slurries B and C were made of hydroxyapatite and that more than 50% of the porous network obtained from the slurry A was made of hydroxyapatite. However, the porous network obtained from the slurry D was not fused by sintering, although it had an appearance similar to those obtained from the slurries A, B and C. The porous network obtained from the slurry D had not satisfactory strength withstanding the practical uses, and collapsed when picked up by fingers.

EXAMPLE 2

A solution of calcium nitrate was added with aqueous ammonium to adjust the pH value thereof to pH 12, to which was added ammonium phosphate until the molar ratio of calcium to phosphor reached 1.67. The precipitate was filtered and washed with water sufficiently to obtain a powder of amorphous calcium phosphate, to which water was added to prepare a slurry A. To 100 parts, by weight, of this slurry A was added 0.5 parts, by weight, of the same foaming agent as used in Example 1 to prepare a slurry B.

A sponge of a polyvinyl polymer having continuous void channels, the average cross-sectional dimension of the channels being 0.1 mm, was dipped into each of the slurries A and B. The sponge was repeatedly compressed and then allowed to expand in each slurry to allow the slurry to get into the channels. By the repeated compression and expansion operations, the slurry B was foamed in the channels of the porous body of the polyvinyl polymer.

After drying at 100° C. for one day, each of the sponges impregnated with slurries A and B was sintered at 1200° C. for one hour to thermally decompose the organic material and concurrently to sinter the particles of calcium phosphate. The pores of the sintered body obtained from the slurry A were discontinuous due to clogging of the slurry. In contrast thereto, the pores of the sintered body obtained from the slurry B were continuous throughout the overall porous body which was made of hydroxyapatite in almost all regions thereof.

EXAMPLE 3

A 0.5% aqueous solution of saponin was coated on each of polyurethane sponges having continuous void channels, the cross-sectional dimensions of which were 3.0, 1.5 and 0.4 mm, and on each of polyvinyl polymer sponges having continuous channels, the cross-sectional dimensions of which were, respectively, 0.05 and 0.04 mm. After repeatedly compressing and then allowing to expand to cover the internal walls of the void channels by aggregated foams, each sponge was squeezed by a roller assembly to remove the excess saponin solution. Then, these sponges were dipped into the slurry prepared in the preceding Example 2 to be impregnated with the slurry, followed by passing through a roller assembly to remove the excess slurry, whereby sponges of polyurethane and the polyvinyl polymer having the walls of the channels impregnated with the slurry were obtained. These sponges were heated at 1300° C. for one hour to decompose and remove the organic materials and concurrently to sinter the inorganic materials.

The porous sintered body produced by using the sponge of vinyl polymer having continuous void channels, the cross-sectional dimension of which was 0.04 mm, included discontinuous portions corresponding to the portions of the channels of the organic sponge material which was not impregnated with the slurry due to fineness of the channels. However, this porous sintered body was useful for some practical applications, and had an average cross-sectional dimension of pores of 0.03 mm and a porosity of 46%.

The porous sintered body produced by using the sponge of polyurethane having continuous void channels, the cross-sectional dimension of which was 3.0 mm, included continuous pores having an average cross-sectional dimension of 2.30 mm and had a porosity of 98%. The network of this porous body was weaker than te other samples, but was judged to be useful for some applications.

The porous sintered bodies produced by using the sponges of polyurethane, the cross-sectional dimensions of which were 1.5 mm and 0.4 mm, respectively and the porous sintered body produced by using the sponge of the polyvinyl polymer, the cross-sectional dimention of which was 0.5 mm, included continuous pores having average cross-sectional dimensions of 1.04 mm, 0.35 mm and 0.03 mm and had porosities of 96%, 92% and 54%. The last-mentioned three porous sintered bodies had strengths enough for withstanding every practical uses.

Although the present invention has been described by referring to specific examples thereof, it should be apparent to those skilled in the art that many modifications and changes may be made without departing from the spirit and scope thereof. The present examples are therefore to be considered in all respects as illustrative and not restrictive. The scope of the invention is limited only by the appended claims, and all changes which come within the meaning and range of equivalency of the claims are to be included therein.

What is claimed is:

1. A process for making a porous sintered body of calcium phosphate having continuous and fine pores distributed uniformly throughout the porous body, comprising the steps of:
   preparing a slurry of amorphous calcium phosphate having a molar ratio of calcium to phosphor ranging within 1.59 to 1.80;
   adding a foaming agent to said slurry;
   dipping a porous body of an organic material having continuous and fine void channels into said slurry prior to or after foaming said slurry to allow said slurry to adhere on the internal walls of said void channels;
   heating said porous body of said organic material at a temperature high enough for decomposing said organic material to varnish into smoke and concurrently for thermally converting said amorphous calcium phosphate into hydroxyapatite to form a network of hydroxyapatite; and
   sintering said network of hydroxyapatite to form said porous sintered body.

2. A process for making a porous sintered body of calcium phosphate as set forth in claim 1, wherein said foaming agent is selected from the group consisting of ionic surfactants, non-ionic surfactants and non-aqueous dispersion medium surfactants.

3. A process for making a porous sintered body of calcium phosphate as set forth in claim 2, wherein said ionic surfactant is selected from the group consisting of fatty acid soaps, alkyl sulfates, straight-chain alkylbenzenesulfonates, quaternary ammonium salts, amine salts and mixtures thereof.

4. A process for making a porous sintered body of calcium phosphate as set forth in claim 2, wherein said non-ionic surfactant is selected from the group consisting of polyoxyethylene alkyl ethers, polyoxyethylene sorbitan monoalkyl esters, sugar esters and mixture thereof.

5. A process for making a porous sintered body of calcium phosphate as set forth in claim 2, wherein said non-aqueous dispersion medium surfactant is selected from the group consisting of fatty acid dodecyl ammonium, sodium dioctylsulfosuccinate and mixtures thereof.

6. A process for making a porous sintered body of calcium phosphate as set forth in claim 1, wherein the cross sectional dimension in every direction of each of said void channels of said porous body of said organic material ranges within 0.05 to 1.5 mm.

7. A process for making a porous sintered body of calcium phosphate as set forth in claim 1, wherein said organic material is selected from the group consisting of polyurethane sponges and sponges of vinyl polymers.

8. A process for making a porous sintered body of calcium phosphate as set forth in claim 1, further comprising a step of putting said porous body of said organic material in an atmosphere of reduced pressure subsequent to said dipping step for allowing said slurry of amorphous calcium phosphate to adhere on the internal walls of said void channels.

9. A process for making a porous sintered body of calcium phosphate as set forth in claim 1, further comprising a step of exposing said porous body of said organic material to ether vapor subsequent to said dipping step for allowing said slurry of amorphous calcium phosphate to adhere on the internal walls of said void channels.

10. A process for making a porous sintered body of calcium phosphate as set forth in claim 1, further comprising a step of subjecting said porous body of said organic material to ultrasonic waves subsequent to said dipping step for allowing said slurry of amorphous calcium phosphate to adhere on the internal walls of said void channels.

11. A process for making a porous sintered body of calcium phosphate as set forth in claim 1, 8, 9 or 10, further comprising a step of applying a centrifugal force to said porous body of said organic material subsequent to said dipping step for allowing said slurry of amorphous calcium phosphate to adhere on the internal walls of said void channels.

12. A process for making a porous sintered body of calcium phosphate as set forth in claim 1, 8, 9 or 10, further comprising a step of applying a compressive force to said porous body of said organic material subsequent to said dipping step for allowing said slurry of amorphous calcium phosphate to adhere on the internal walls of said void channels.

13. A process for making a porous sintered body of calcium phosphate as set forth in claim 1, wherein said slurry of amorphous calcium phosphate is prepared by the wet synthesis method to obtain a liquid containing amorphous calcium phosphate which is subjected to the dehydration or drying step followed by the step of adding with a dispersion medium.

14. A process for making a porous sintered body of calcium phosphate as set forth in claim 1, wherein said heating step is effected at a temperature higher than 800° C.

15. A process for making a porous sintered body of calcium phosphate as set forth in claim 1, wherein the cross sectional dimension in every direction of each of said pores ranges within 0.03 to 1.2 mm and the porosity of said porous sintered body of calcium phosphate ranges within 40 to 97%.

* * * * *